United States Patent [19]

Matthiessen

[11] Patent Number: 4,663,958
[45] Date of Patent: May 12, 1987

[54] METHOD FOR SENSITIZING AND STABILIZING THE OPERATING CONDITION OF A SEMICONDUCTOR GAS SENSOR AND A SEMICONDUCTOR GAS SENSOR DEVICE THEREFOR

[75] Inventor: Hans Matthiessen, Gross Parin, Fed. Rep. of Germany

[73] Assignee: Drägerwerk Aktiengesellschaft, Lübeck, Fed. Rep. of Germany

[21] Appl. No.: 826,900

[22] Filed: Feb. 6, 1986

[30] Foreign Application Priority Data

Feb. 9, 1985 [DE] Fed. Rep. of Germany ....... 3504499

[51] Int. Cl.⁴ .......................................... G01N 27/12
[52] U.S. Cl. .......................................... 73/1 G; 73/23
[58] Field of Search ................ 73/1 G, 23, 27 R; 338/34; 324/71.5; 340/634; 422/98

[56] References Cited

U.S. PATENT DOCUMENTS

| | | | |
|---|---|---|---|
| 3,421,362 | 1/1969 | Schaeffer | 73/23 |
| 3,495,437 | 2/1970 | Estes, III et al. | 73/1 G |
| 3,824,836 | 7/1974 | Lyshkow | 73/1 G |
| 3,864,628 | 2/1975 | Klass et al. | 73/23 X |
| 3,960,495 | 6/1976 | Tantram | 73/27 R X |
| 4,112,736 | 9/1978 | Wheldon et al. | 73/23 |
| 4,151,738 | 5/1979 | Hyer et al. | 73/1 G |
| 4,288,774 | 9/1981 | Takomi et al. | 338/34 |
| 4,399,684 | 8/1983 | Advani et al. | 73/1 G |

FOREIGN PATENT DOCUMENTS

| | | | |
|---|---|---|---|
| 3116244 | 4/1982 | Fed. Rep. of Germany. | |
| 3126647 | 1/1983 | Fed. Rep. of Germany | 73/1 G |
| 152416 | 11/1981 | German Democratic Rep. | 73/23 |
| 6800 | 2/1972 | Japan | 73/1 G |
| 17387 | 2/1978 | Japan | 73/1 G |
| 124790 | 9/1979 | Japan | 73/1 G |

OTHER PUBLICATIONS

"Thick-Film CO Gas Sensors"; *IEEE Transactions on Electron Devices*, vol. ED-26, No. 3, pp. 247-249, Mar. 1979; Masayoshi Nitta et al.

Primary Examiner—Stewart J. Levy
Assistant Examiner—Tom Noland
Attorney, Agent, or Firm—Walter Ottesen

[57] ABSTRACT

When in use for a relatively long time and during the period of operational readiness, semiconductor gas sensors for measuring gas components of a gas mixture exhibit decreasing sensitivity and increased aging, so that if a relatively large quantity of the gas component that is to be measured is encountered they emit either no signal at all or at least an overly feeble signal. A method is disclosed to improve sensitivity and to attain a rapid reaction to the gas that is to be measured. The method is performed by continuously exposing the sensor to a stabilizing concentration having a defined amount of the gas component that is to be measured, particularly during absence of the gas component that is to be measured. A sensor wherein the method of the invention is carried out is also disclosed.

8 Claims, 1 Drawing Figure

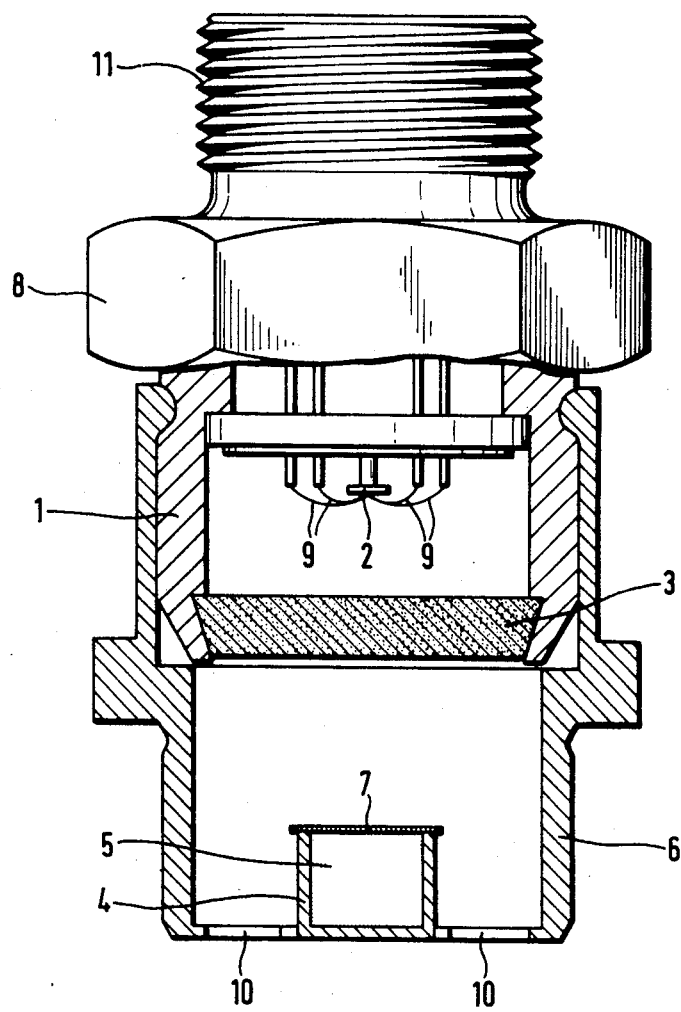

METHOD FOR SENSITIZING AND STABILIZING THE OPERATING CONDITION OF A SEMICONDUCTOR GAS SENSOR AND A SEMICONDUCTOR GAS SENSOR DEVICE THEREFOR

FIELD OF THE INVENTION

The invention relates to a method for sensitizing and stabilizing the operating condition of semiconductor gas sensors for measuring a component in a gas mixture. A semiconductor gas sensor device for performing the method is also disclosed.

BACKGROUND OF THE INVENTION

Gas sensors are known for measuring a gas component in a gas mixture using semiconductor means. These gas sensors measure the gas concentration by changes which occur in the surface conductivity thereof; this is caused by adsorption on the semiconductor surface of the gas component that is to be measured. To increase the sensitivity of the semiconductor sensors, metallic admixtures are for instance added to the sensors. Specific admixtures of metallic substances produce a specific sensitivity of the semiconductor sensor to a gas component that is to be measured. However, if this gas component that is to be measured does not occur for a relatively long period in the gas mixture in which the semiconductor is located, then the semiconductor loses its sensitivity. To overcome this, the semiconductor sensor is for instance exposed briefly to a small quantity of the gas component that is to be measured, which causes its sensitivity to increase once again.

If a fresh, still unused semiconductor sensor is repeatedly exposed during its period of operation to the gas component that is to be measured, its sensitivity can initially decrease before it attains a stable final value. The semiconductor sensor ages. Such aging can be performed artificially with fresh semiconductor sensors before they are installed at the location where they will be used for measurement.

A method for stabilizing semiconductor gas sensors of the type referred to above is disclosed in German published patent application DE-OS No. 31 16 244. In the known method, the semiconductor gas sensor is introduced once into a gas atmosphere that contains the gas component that is to be measured at the location where the semiconductor gas sensor is later installed.

This type of aging method requires only that the semiconductor gas sensor, before it is installed, be exposed to the gas component that is to be measured and which is at a more or less high gas concentration. The aging of a semiconductor sensor is a long-term process, however, and it is not completed after a single performance of the known method. Furthermore, a relatively long period may elapse, even for an aged sensor, between its installation and the first time that the presence of the gas component that is to be measured occurs. In the meantime, the sensor continues to lose sensitivity because it has not been exposed to the gas component that is to be measured for a relatively long period. Even a semiconductor sensor that is already installed at the location where measurement will be performed would have to be exposed repeatedly to the gas component that is to be measured, if there are long intervals between measurements. However, a method of this type would require a substantial effort, because a semiconductor gas sensor that has already been installed would have to be exposed periodically, via a calibrating device disposed elsewhere than at the measurement location, to a predetermined gas concentration of the gas component that is to be measured.

SUMMARY OF THE INVENTION

It is an object of the invention to provide an improved method of the above-mentioned type for sensitizing and stabilizing the operating condition of sensors so as to ensure an unvarying sensitivity and a rapid reaction of the semiconductor sensor when the presence of the gas component that is to be measured occurs.

The method of the invention realizes the above object by exposing the sensor continuously, in particular during the absence of the gas component that is to be measured, to a stabilizing concentration of a fixed amount of the gas component that is to be measured.

The method according to the invention assures a constant and uniform activation of the semiconductor gas sensor during its entire period of operational readiness, thereby making a reliable indication of the sensitivity of the semiconductor gas sensor possible. A separate, self-contained calibrating device is no longer necessary. In addition, aging, which loses its effectiveness during and after the installation of the semiconductor sensor at the measurement location, no longer needs to be performed by the semiconductor manufacturer.

Preferably the stabilizing concentration of the gas component that is to be measured is fixed at a level below the response sensitivity of the sensor. Practical experimentation has shown that such a concentration effects an optimal sensitization.

In another embodiment of the invention, the stabilizing concentration can be just above the response sensitivity of the sensor, so that a continuous base value is measured and used as a reference signal for evaluating the gas component that is to be measured in a gas mixture. With this embodiment, an increase in the reproducibility of measured values is obtained.

To this end, the stabilizing concentration should advantageously be adjusted to a level such that it amounts to 1/20 of the measurement range of the measuring apparatus.

A suitable embodiment of a sensor which can be stabilized and sensitized by the method according to the invention has a sensor housing wherein small quantities of the gas component that is to be measured arrive at the semiconductor sensor, via a diffusion membrane, from a container holding the stabilizing concentration.

BRIEF DESCRIPTION OF THE DRAWING

The invention will now be described with reference to the drawing which shows a side elevation view of a sensor device according to the invention. The sensor device is partially in section to show the components disposed therein.

DESCRIPTION OF THE PREFERRED EMBODIMENT OF THE INVENTION

The drawing shows a sensor housing 1 wherein the semiconductor 2 is mounted on a base plate 8. A plurality of leads 9 extend out of the sensor housing 1 to a measuring apparatus, not shown. The sensor housing 1 is partitioned off from the interior of a surrounding housing 6 by a sintered metal disk 3. A container 4 is closed off in the direction facing toward the sensor housing 1 by a porous membrane 7 and is located in the surrounding housing 6. The gas component that is to be measured is disposed in the interior of the container 4 in the form of a charge 5 to produce the stabilizing concentration.

The sensor according to the invention includes a plate 8 on which is formed a threaded portion 11. When the sensor is used, the sensor housing 1 is secured by means of its threaded portion 11 to a measurement location with the openings 10 of the surrounding housing 6 protruding into the gas mixture that is to be tested.

As long as gas diffuses continuously out of the container 4, especially while the gas component that is to be measured is absent, the sensor 2 is sensitized and stabilized. If a relatively large quantity of the gas component that is to be measured occurs in the gas mixture, then the sensor 2, which is sensitized and stabilized as described above, supplies a signal of high amplitude and with very steep edges to the measurement apparatus.

It is understood that the foregoing description is that of the preferred embodiments of the invention and that various changes and modifications may be made thereto without departing from the spirit and scope of the invention as defined in the appended claims.

What is claimed is:

1. Method for sensitizing and stabilizing the operating condition of a semiconductor gas sensor for measuring a component in a gas mixture, the method comprising continuously exposing the sensor to one stabilizing concentration of the gas component to be measured during the absence of said component, wherein said sensor supplies signals to a measuring apparatus, said stabilizing concentration having a magnitude sufficient to cause said sensor to supply a signal to the measuring apparatus which serves as a reference signal for the measurement of said gas component.

2. The method of claim 1, said stabilizing concentration being below the response sensitivity of the sensor.

3. The method of claim 1, wherein said stabilization concentration of the gas component to be measured constitutes a 1/20 part of the measuring range of said measuring apparatus.

4. A semiconductor gas sensor device for measuring a gas component in a gas mixture, the semiconductor gas sensor device comprising:
a housing;
a partition wall for partitioning said housing into two compartments;
a semiconductor sensor mounted in one of said compartments;
gas dispensing means mounted in the other one of said compartments for dispensing a stabilizing concentration of said gas component into said other compartment; and,
said partition wall being porous for permitting said stabilizing concentration to pass therethrough into said one compartment for sensitizing and stabilizing said semiconductor sensor.

5. The semiconductor gas sensor device of claim 4, said gas dispensing means comprising: a vessel for receiving a charge of said gas component for generating said stabilizing concentration; and, a porous membrane covering said vessel and through which the interior of said vessel communicates with said other compartment.

6. A semiconductor gas sensor device for measuring a gas component in a gas mixture, the semiconductor gas sensor device comprising:
a housing;
membrane means for partitioning said housing into two compartments;
a semiconductor sensor mounted in one of said compartments;
gas dispensing means mounted in the other one of said compartments for dispensing a stabilizing concentration of said gas component into said other compartment; and,
said membrane means being porous to permit said stabilizing concentration to migrate from said other compartment to said one compartment for sensitizing and stabilizing said semiconductor sensor.

7. A semiconductor gas sensor device for measuring a gas component in a gas mixture, the semiconductor gas sensor device comprising:
a housing having an outer wall defining an interior space;
a partition wall for partitioning said housing and said space into two compartments;
a semiconductor sensor mounted in one of said compartments;
gas dispensing means mounted in the other one of said compartments for dispensing a stabilizing concentration of said gas component;
said partition wall being porous for permitting said stabilization concentration to pass therethrough into said one compartment for sensitizing and stabilizing said semiconductor; and,
aperture means formed in said outer wall and communicating with the porous partition wall via said other compartment for conducting said gas mixture from the ambient into said other compartment thereby facilitating the passage of said gas mixture through the porous partition wall to said sensor.

8. The semiconductor sensor device of claim 7, comprising attachment means formed on said housing for attaching said device at a location where the measurement of said gas mixture is to be made.

* * * * *